United States Patent [19]

Arpagaus et al.

[11] Patent Number: 4,830,832
[45] Date of Patent: May 16, 1989

[54] PIPETTE AND PIPETTING APPARATUS

[75] Inventors: Renato Arpagaus, Chur; Herwig Leyssens, Tamins, both of Switzerland

[73] Assignee: Hamilton Bonaduz AG, Bonaduz, Switzerland

[21] Appl. No.: 941,088

[22] Filed: Dec. 12, 1986

[30] Foreign Application Priority Data

Dec. 17, 1985 [CH] Switzerland .................. 5394/85

[51] Int. Cl.⁴ .................................. G01N 35/06
[52] U.S. Cl. .......................... 422/65; 73/864.13; 73/864.17; 422/63; 422/100
[58] Field of Search .............. 422/65, 64, 63, 100; 73/864.13, 864.14, 864.16, 864.17, 863.32

[56] References Cited

U.S. PATENT DOCUMENTS

| 3,444,742 | 5/1969 | Ellis et al. | 73/863.32 |
|---|---|---|---|
| 3,832,135 | 8/1974 | Drozdowski | 436/49 |
| 4,041,764 | 8/1977 | Sabloewski et al. | 73/863.14 |
| 4,198,483 | 4/1980 | Sozi et al. | 422/63 |
| 4,341,736 | 7/1982 | Drbal et al. | 422/63 |
| 4,418,580 | 12/1983 | Satchell et al. | 73/864.14 |
| 4,478,095 | 10/1984 | Bradley et al. | 422/64 |
| 4,567,780 | 2/1986 | Oppenlander et al. | 422/100 |
| 4,616,514 | 10/1986 | Magnussen, Jr. et al. | 73/869.14 |
| 4,681,742 | 7/1987 | Johnson et al. | 422/65 |

FOREIGN PATENT DOCUMENTS

6504453 10/1966 Netherlands .................. 73/863.32

Primary Examiner—Michael S. Marcus
Attorney, Agent, or Firm—Burgess, Ryan & Wayne

[57] ABSTRACT

A pipette includes a pipette body made of plastic material and a pipette piston made of plastic material that is also electrically conductive. The pipette is automatically received or discarded in a pickup device which has an electric transmission filament. A pipetting apparatus has a pickup device for receiving test containers, a pickup section for a microstandard plate, a pipette hopper, and a dosing device. For automatic pipetting, the dosing device receives the pipettes, conveys the pipettes while simultaneously changing the distance of the pipettes to the test containers, absorbs liquid through the pipette, conveys the pipettes while simultaneously changing the distance of the pipette to the microstandard plate, discharges the liquid, and finally ejects the pipette.

9 Claims, 9 Drawing Sheets

PIPETTE AND PIPETTING APPARATUS

BACKGROUND OF THE INVENTION

This invention concerns a pipette including a pipette body and a pipette piston, a pickup device with a pipette, and a pipetting apparatus with a pickup device.

Many different pipettes are known, generally having a pipette body and a pipette piston. The pipettes are either manually utilizable or are mounted in pipette apparatus.

Pipette apparatus are also known in which at least one tip, each at a predetermined distance from the other, is used for pipetting. The tips are mounted on a bracket or the like and can be moved between two positions without changing the distance between the tips. The solution to be pipetted is delivered by a peristaltic pump. Such apparatus can separately pick up the tips, or a certain number of so-called ratchets which are mounted by hand can be used. Since the distance between the tips is retained during the pipetting operation, the samples to be pipetted must be arranged in the same pattern as the reaction vessel. This can be disadvantageous.

OBJECTS AND SUMMARY OF THE INVENTION

It is an object of the invention to provide a pipette having a pipette body and a pipette piston utilizable as a one-way pipette in an automatic pipetting operation.

This object is attained by the characteristic features set forth herein.

Further, since at least one part of the pipette is electrically conductive, each pipette can be used as a liquid detector.

Also, both the pipette body and the pipette piston can be provided with a section in order to accommodate the pipette in a pickup device, the sections constituting parts of a stretch coupling.

A pickup device according to the invention is characterized by the features described herein. The advantages of such a device are that the pipette body and the pipette piston can be separately and automatically engaged and released and moved relative to each other by first and second assemblies of the pickup device.

In a preferred embodiment of the pickup device, the first and second assemblies are constructed as outer and inner collets having an adapter sleeve and a gripping element to pick up the pipette body and the pipette piston, and the inner collet is movably disposed in the outer collet. Means are provided whereby the collets can be joined to the pipette body in order, when the pipette is picked up, to press the pipette body against a stop and the pipette piston in the foremost position, and when the pipette is released, to push the pipette piston together with the pipette body toward the pickup device.

A pipetting apparatus according to the invention is characterized by the features described herein.

The advantages of the apparatus are to be essentially seen in that the pipettes can be selectively and automatically picked up; the test containers can be separately lifted; it is possible directly to pipette from the test containers, and assembly with vessels that are arranged in a regular pattern such as microstandard plates.

The pipettes are ejected after the pipetting operation; and the pipetting operation is substantially shortened.

The above and other objects, features and advantages of the present invention will become readily apparent from the following detailed description which is to be read in connection with the accompanying drawings.

DETAILED DESCRIPTION OF THE PREFERRED EMBODIMENT

Figure 1:
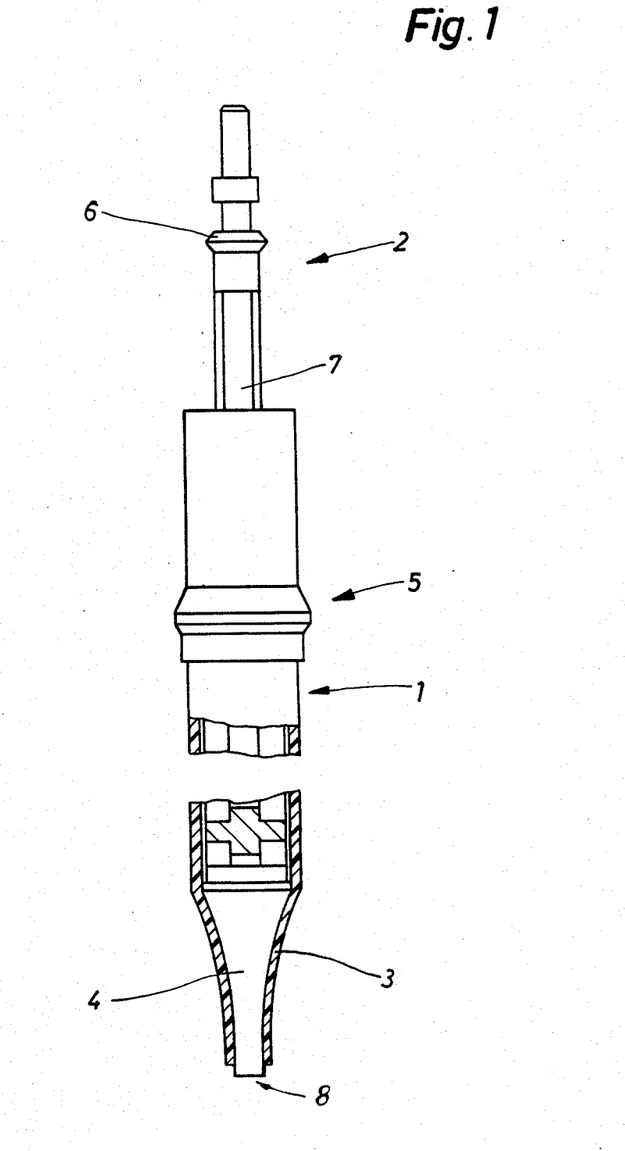
FIG. 1 is an elevational view, partly broken away of one embodiment of a pipette according to the present invention.

The pipette according to FIG. 1 comprises a pipette body 1 and a pipette piston 2. Preferably, pipette body 1 is made of a plastic material, and pipette piston 2 likewise is made of a plastic material which is also electrically conductive. Pipette body 1 is tubular and has an end section 3 that substantially conically tapers and serves as a suction tip. Pipette piston 2 has a substantially conical end section 4, the configuration of which is adapted to fit within end section 3 of pipette body 1 so that pipette body 1 and pipette piston 2 form a unit free of clearance volume. End section 4 of pipette piston 2 is shaped in a manner such that a section 8 thereof projects from pipette body 1 when pipette piston 2 is fully inserted in pipette body 1.

Pipette body 1 also has an annular section 5 formed around a peripheral section thereof. In like manner, pipette piston 2 has an annular section formed about the opposite end section thereof. As will be explained in connection with FIGS. 2a to 2d, annular sections 5 and 6 form parts of plug couplings. Preferably, the stem 7 of pipette piston 2 has a cruciform cross-sectional shape and tapers starting from conical end section 3 although stem 7 can have a different cross-sectional shape.

Figure 2A:
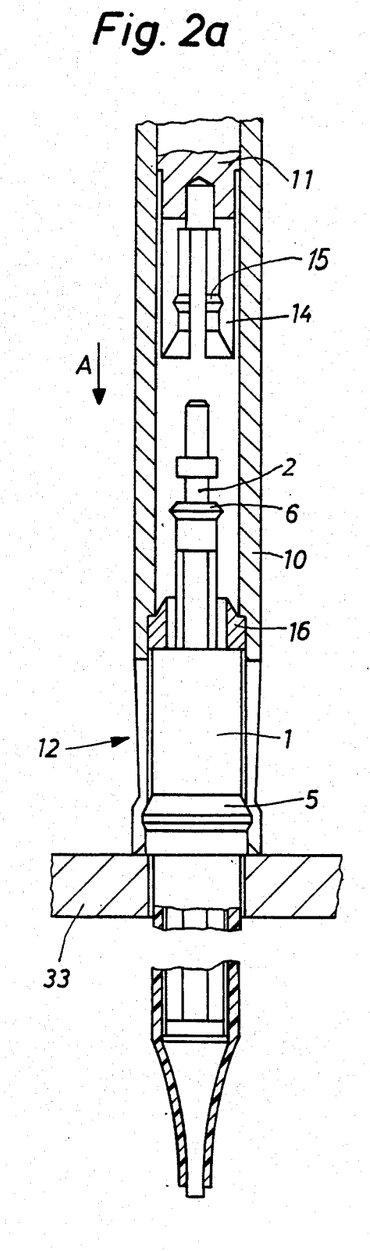
FIGS. 2a to 2d are elevational cross-sectional views of one embodiment of a pickup device according to the present invention for a pipette according to FIG. 1, in four working positions.
Figure 2B:
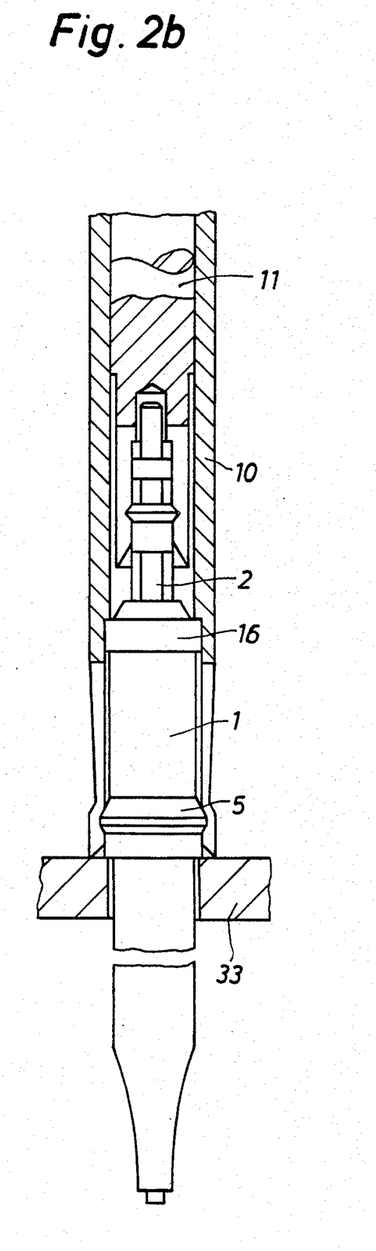
Figure 2C:
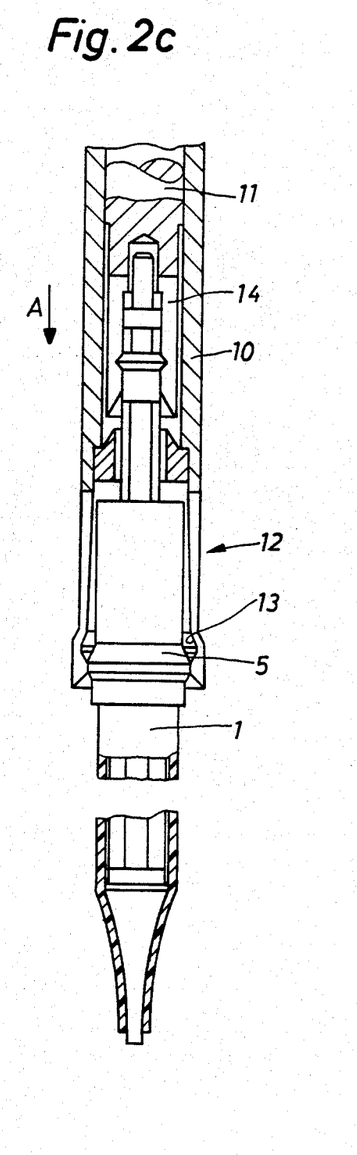
Figure 2D:
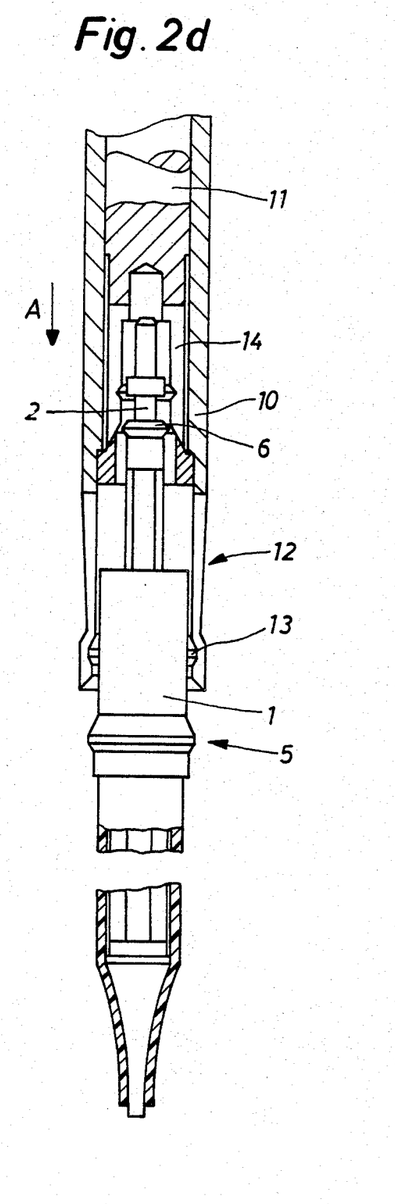

In FIGS. 2a to 2d, there is shown, in four positions, an embodiment of a pickup device for the pipette according to FIG. 1, namely, with accomodated pipette body 1 (FIG. 2a), with accommodated pipette piston 2 (FIG. 2b), with partly ejected pipette body 1 (FIG. 2c) and with partly ejected pipette piston 2 (FIG. 2d).

As the Figures show, the pickup device has a first gripping element 10, which is tubular, and a second gripping element 11, which is rod-shaped and situated within first gripping element 10. First gripping element 10 has a slotted end section 12 which is interiorly provided with an annular recess 13 (FIGS. 2c and 2d) having a configuration similar to and adapted to receive annular section 5 on the periphery of pipette body 1. Second gripping element 11 likewise has a slotted end section 14 which is interiorly provided with an annular recess 15 (FIG. 2a) having a configuration similar to and adapted to receive annular section 6 on the other end section of pipette piston 2. An expanding sleeve 16 is also situated within first gripping element 10. In addition, first and second gripping element 10 and 11 have on opposite ends thereof, means for mounting them in a pipetting apparatus.

First and second gripping element 10 and 11 are made of metal and are insulated from each other by means which are not shown. In this manner, pipette piston 2 and second gripping element 11 form an electric conductor.

In operation, pipettes of the type shown in FIG. 1 are held in a slide 33 (to be described later). By moving first gripping element 10 in the direction of arrow A, its end section 12 is moved with respect to pipette body 1 until annular section 5 on pipette body 1 meshes in annular recess 13 in end section 12. Thus, end section 12 and annular section 5 on the periphery of pipette body 1 form part of a plug coupling, as shown in FIGS. 2a and 2b. After pipette body 1 has been engaged by first gripping element 10, pipette piston 2 is engaged by moving second gripping element 11 in the direction of arrow A. This operation terminates when annular section 6 on pipette piston 2 meshes with annular recess 15 of second gripping element 11. Similarly, as with first gripping element 10, end section 14 and annular section 6 on pipette piston 2 form parts of a plug coupling, as shown in FIG. 2b. If the pipette is engaged by first and second gripping element 10 and 11, a pipetting operation can be carried out with the pipette. After the pipetting operation, the pipette is ejected.

As FIG. 2c shows, pipette body 1 is first ejected from first gripping element 10 while second gripping element 11 is moved in the direction of arrow A and first gripping element 10 is held in position. By further moving second gripping element 11 in the direction of arrow A, slotted end section 14 of second gripping element 11 is pressed against the expanding sleeve 16 and simultaneously expanded. Due to this expanding, pipette body 2 is released so that the pipette drops out from the pickup device.

Figures 3, 4, 5A, 5B:
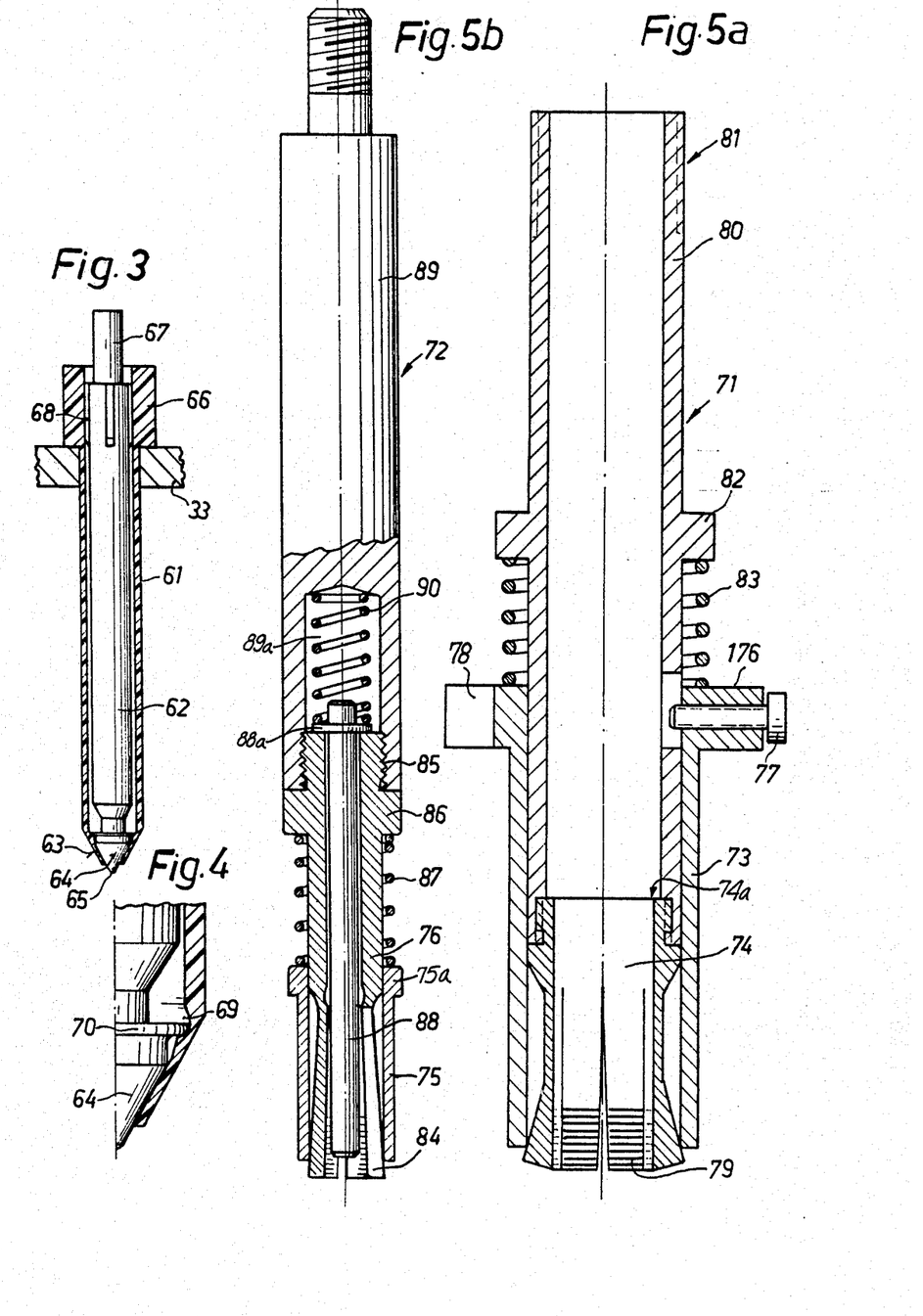
FIG. 3 is an elevational cross-sectional view of a preferred embodiment of a pipette according to the present invention.
FIG. 4 is a cross-sectional view thruugh the suction tips of the pipette of FIG. 3.
FIGS. 5a and 5b are elevational cross-sectional views of inner and outer collets, disassembled, of a pickup device according to the present invention for use with the pipette according to FIG. 3.

The pipette shown in FIGS. 3 and 4 also comprises a pipette body 61 and a pipette piston 62. Preferably, pipette body 61 is made of a plastc material and pipette piston 62 is made of an electrically conductive plastic material. It is advantageous if pipette body 61 is made of polypropylene and pipette piston 62 of polyethylene with added graphite. Pipette body 61 is tubular and has a substantially conical end section 63 built as a suction tip. Pipette piston 62 is rod-like and has a substantially conical end section 64 which is similar in configuration to and adapted to fit within the interior space of end section 63 of pipette body 61 so that pipette body 61 and pipette piston 62 form in the area of suction tip 63 a unit free of clearance volume. End section 64 of pipette piston 62 is, in addition, constructed in a manner such that a section 65 thereof, projects from pipette body 61 when pipette piston 62 is fully inserted within pipette body 61. Pipette body 61 has on its other end, an annular section 66 that forms a pickup section and is formed on the periphery of body 61 and is provided with an edge. The opposite end section 67 of pipette piston 62 is cylindrical, and adjacent to end section 67, there are formed four radially projecting sections 68 to center pipette piston 62 in pipette body 61.

The end section 63 of pipette body 61 that forms the suction tip has less wall thickness than the tubular section of pipette body 61 that is adjacent thereto. By an adequate construction, the shrinkage operation can be advantageously affected so as to provide in pipette body 1, an extension 69 in the transition area between end section 63 and the tubular portion of body 61. On pipette piston 62, adjacent end section 63 that forms the suction tip, there is formed a flange-like sealing lip 70, which is inside the extension within pipette body 61 when piston 62 assumes the foremost position in pipette body 61.

Annular section 66 and cylindrical end section 67 of pipette piston 62 form pickup sections, as will be explained in connection with FIGS. 5a and 5b.

In FIGS. 5a and 5b, there is shown a preferred embodiment of the pickup device for the above described pipette. Specifically, the pickup device has an outer collet 71 and an inner collet 72, respectively, shown for better understanding, in separate FIGS. 5a and 5b. Inner collet 72, shown in FIG. 5b, is to be situated inside outer collet 71. Outer and inner collets 71 and 72 each have an adapter sleeve 73 and 75 and a gripping element 74 and 76, respectively. Adapter sleeve 73 of outer collet 71 has a tubular shape and on one end, has an attachment 176 with a screw 77 for connecting an electric line (not shown) and a recess 78 to prevent rotation of the pickup device in the pipetting apparatus. Gripping element 74 of outer collet 71 is tubular and is provided at one end with a clamping section 79 that interacts with the adapter sleeve 75 in order to firmly clamp inner collet 72. Gripping element 74 is screwed at the other end on an end of an extension pipe 80. On the other end, extension pipe 80 has a section 81 provided with an external thread. Extension pipe 80 has in addition, an annular attachment 82 formed on the periphery thereof, and spaced from one end. Gripping element 74 and extension pipe 80 are situated within adapter sleeve 73 in a manner such that extension pipe 80 projects from the end of adapter sleeve 73 provided with attachment 176. Between attachment 176 of adapter sleeve 73 and attachment 82 of extension pipe 80, there is situated on extension pipe 80, a compression spring 83 which draws gripping element 74 into adapter sleeve 73.

Inner collet 72 is shaped similarly to outer collet 71 within adapter sleeve 73. In adapter sleeve 75, there is situated a gripping element 76, having on one end thereof a clamping section 84 and on the other end, a section 85 provided with an external thread. A bead 86 is, in addition, formed on the periphery of gripping element 76 near threaded section 85. Between the end of adapter sleeve 75 and bead 86, there is situated on gripping element 76, a compression spring 87 that draws gripping element 76 into adapter sleeve 75. Within gripping element 76, there is positioned an ejector 88, which is movable into gripping element 76 when collet 72 is open. There is also screwed on threaded section 85 of gripping element 76, an extension pipe 89 in order to make it possible to connect collet 72 with the pipetting apparatus. Extension pipe 89 is provided with a blind hole 89a. Within connecting pipe 89, is situated another compression spring 90 that prestresses ejector 88 in the direction toward the gripping portion of collet 72. Spring 90 has one end that abuts against the bottom (upper end) of blind hole 89a and an opposite end that abuts against a flange portion 88a of ejector 88.

Outer and inner collets 71 and 72 are made of metal and can be electrically insulated from each other by suitable means (not shown). In this manner, the pipette piston and the inner collet form an electric conductor.

Figure 6A:
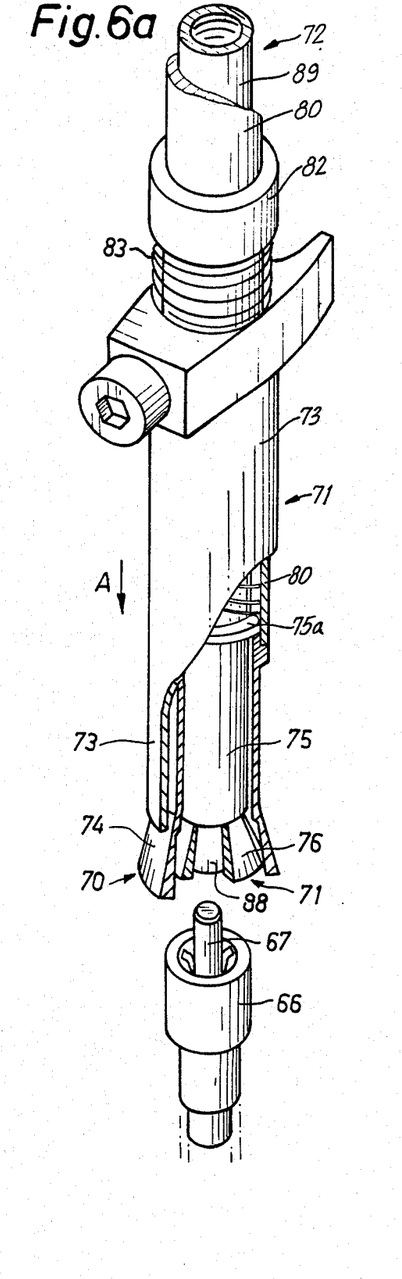
FIGS. 6a to 6d are perspective, partially broken away views of the pickup device of FIGS. 5a and 5b in four working positions.
Figure 6B:
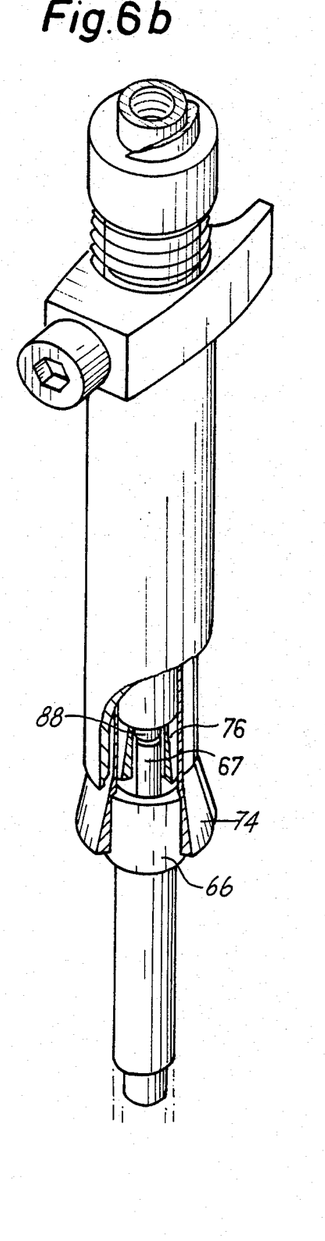
Figure 6C:
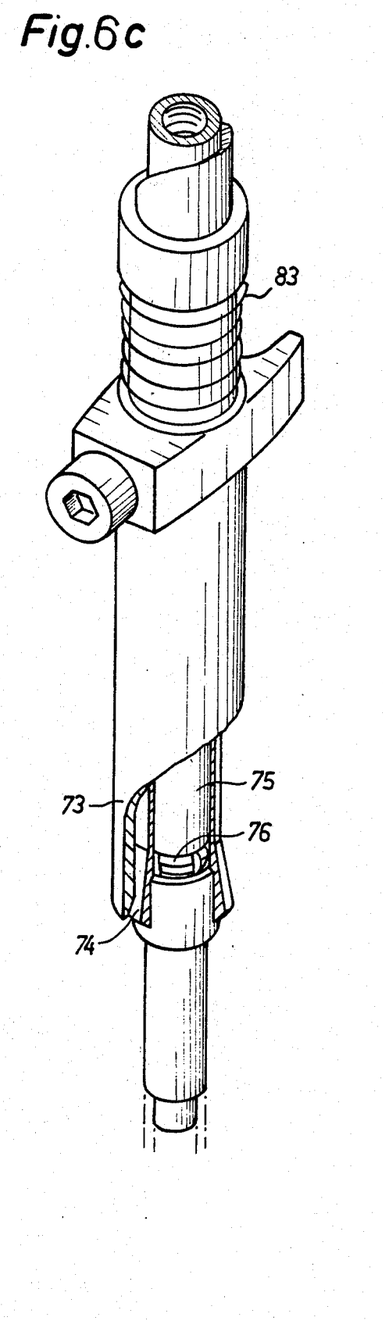
Figure 6D:
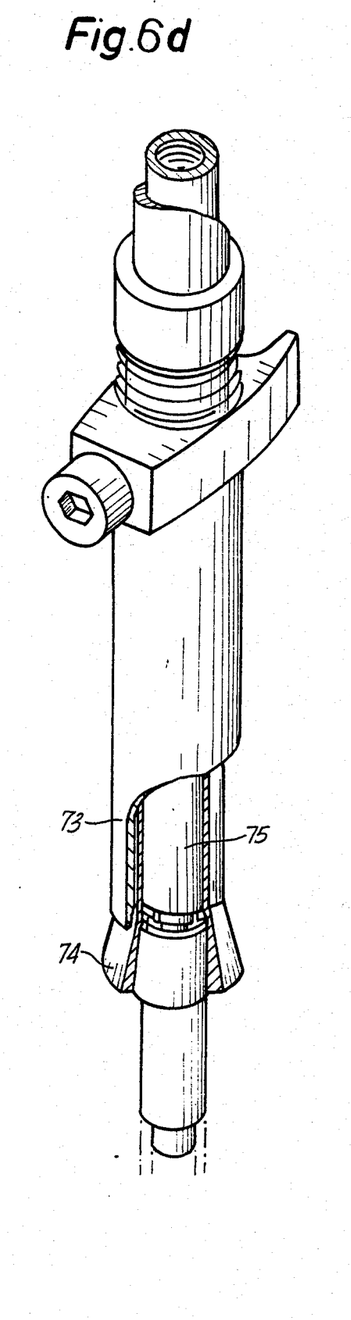

In operation, in a slide 33 to be described later, there are supported pipettes with the construction shown in FIG. 3. The pickup device with open collets 71 and 72 (FIG. 6a) is displaced toward the pipette in the direction of arrow A. Collets 71 and 72 are opened by reason that gripping elements 74 and 76 are pushed out from their adapter sleeves 73 and 75 against the force of compression springs 83 and 87. If collets 71 and 72 are open, ejector 88 can be displaced against the force of compression spring 90. When the pickup device with open collets is moved toward the pipette, ejector 88 pushes toward the front face of end section 66 of pipette piston 62 and with the force of compression spring 90, presses pipette piston 62 into the foremost positon in pipette body 61 and thereby presses pipette body 61 against slide 33. Consequently, there is no clearance volume present in the suction tip and the pipette always assumes the same position for the pick up. Inner collet 72 is then drawn back and end section 67 of pipette piston 62 is gripped and firmly clamped by gripping element 76 (FIG. 6b). Outer collet 71 is subsequently drawn back and end section 66 of pipette body 61 is gripped and firmly clamped by gripping element 74 (FIG. 6c). Thus, the pipette is accommodated and a dosing operation can be carried out. After dosing, outer collet 71 is first opened by pushing gripping element 74 against the force of compression spring 83. As a result, end section 66 of pipette body 61 is released. In this position, pipette body 61 is retained by pipette piston 62 (FIG. 6d). Thereafter, inner collet 72 is opened by moving adapter sleeve 75 against the force of compression spring 87. In this position, the entire pipette is now ejected by ejector 88 prestressed by compression spring 90. Thus, the pickup device resumes the position shown in FIG. 6a.

Figure 7:
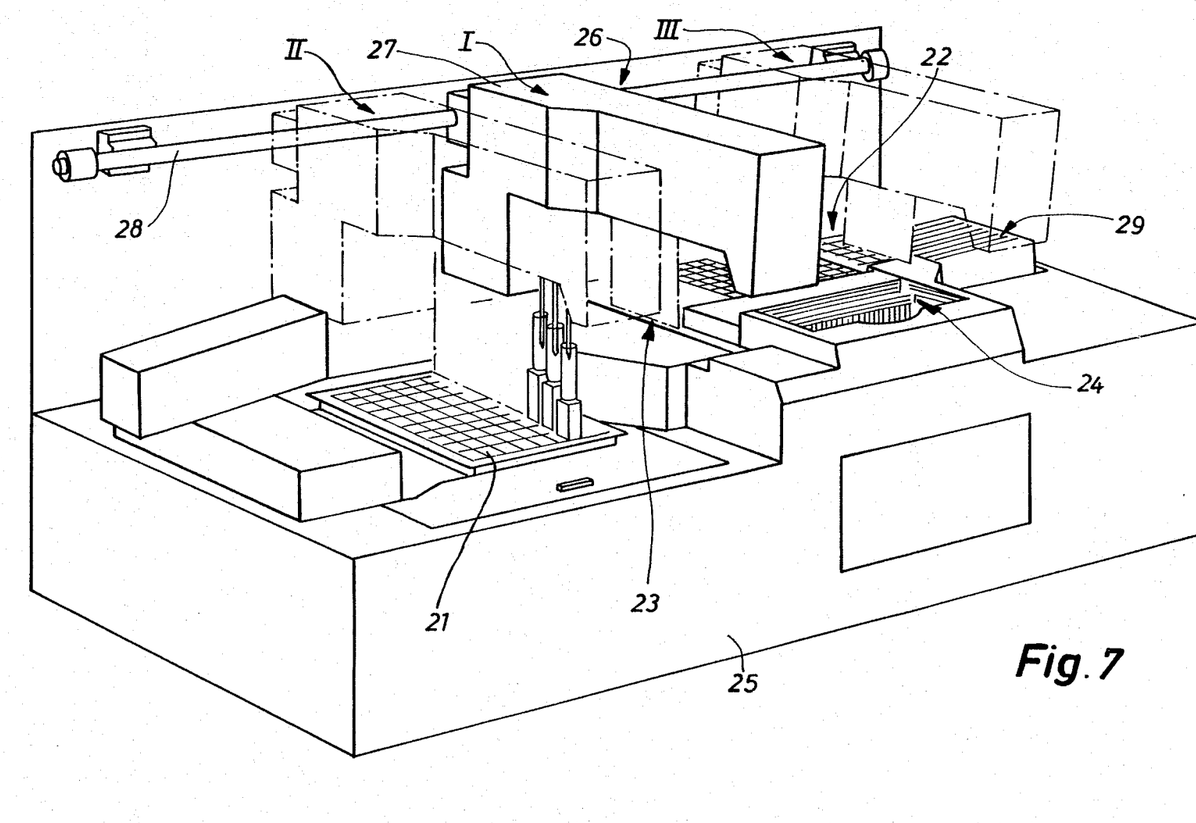
FIG. 7 is a perspective view of an embodiment of a pipetting apparatus according to the present invention.

In FIG. 7 is shown a pipetting apparatus in which the above described pipettes and pickup devices are used to make it possible to carry out a multiple pipetting operation. FIG. 7 shows the pipetting apparatus in three positions for performing the pipetting operation, namely, position I in which the pipettes are received or ejected; position II in which the liquid is received by the pipettes, and position III in which the liquid is delivered by the pipettes.

The pipetting apparatus includes a receiving device 21 for the test containers, pickup section for one or more microstandards or Abott plates 22, a receiving device 29 for containers for storage of reagents, a feeding device 23 for the pipettes and a pipette hopper 24, which are situated side by side in a chassis 25 and are accessible from above. The pipetting apparatus contains, in addition, a dosing device 26 situated in a frame 27 movable above chassis 25, frame 27 being guided in a rail 28 and being moved along rail 28 by a drive unit (not shown). Other details of the dosing device are described with reference to FIGS. 9 and 10.

Figure 8:
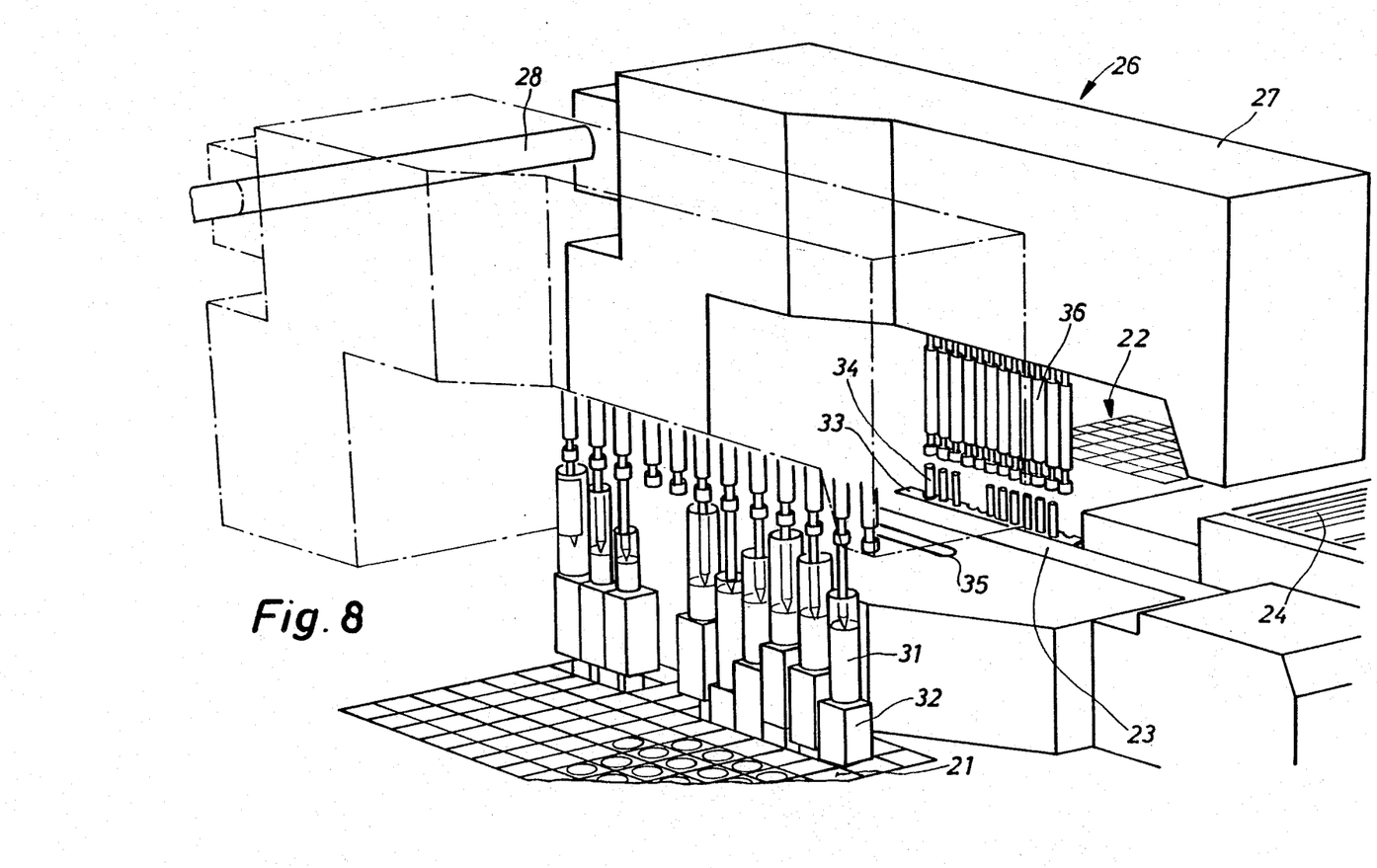
FIG. 8 is a perspective view showing a segment of the apparatus of FIG. 7, in enlarged scale.

As seen from FIG. 8 which shows a segment of the representation in FIG. 7, receiving device 21 can accommodate a plurality of test containers 31. In the pipetting apparatus here in question, there are provided ninety-six test containers that can be inserted in receiving device 21 in eight rows of twelve containers. Each test container 31 is situated in a support 32 which advantageously contains a collet in order advantageously to hold the container positionally stable and to enable use of different test containers. Receiving device 21 additionally includes a drive means (not shown) for moving test containers 31 relative to dosing device 26. This drive means comprises twelve drive units disposed in a row and coordinated with each support 32 and an additional drive unit to move the twelve drive units together. The movement of each support 32 is controlled by detectors, that is, by the respective electrically conductive pipette piston. Pickup device 21 for test containers 31 is designed so as to make it possible to insert test containers having an outer diameter of from 10 to 17 mm and a length of 100 mm.

A plurality of pipettes 34 are stored in pipette hopper 24. The pipettes are contained in a support element (not shown) which has from one to seven U-shaped chambers in which there are received each time, 36 pipettes in one row, the pipettes with the end section 67 of the pipette body being movably arranged in said chambers. Due to the U-shape of the support elements, the pipettes can be advantageously inserted without contact in the pipette hopper.

Feeding device 23 contains a conveyor to transport the support elements with the pipettes from pipette hopper 24, a displacement device that transports the pipettes from the support elements and a delivery device that takes over the pipettes from the displacement device and prepares them to be received by the pickup device.

The conveyor essentially comprises a drive unit and an endless belt driven thereby which grasps the support elements with the pipettes. The displacement device contains a drive unit and an eccentrically driven ratchet that envelops the pipettes and each time relays one pipette to the delivery device. The delivery device has a drive unit and a slide 33 with a number of notches formed in a row. The eccentrically driven ratchet and slide 33 are disposed forming a right angle so that the pipette that is directly in front of the slide, is pushed by the ratchet into a notch of the slide. Depositing of the pipettes onto slide 33 is controlled by a control apparatus. As seen from FIG. 8, nine of twelve possible notches are only covered, although this will vary. Between receiving device 21 and feeding device 23, there is provided a cleaning device 35 to cleanse the pipettes after the liquid has been aspirated from the test containers.

Figure 9:
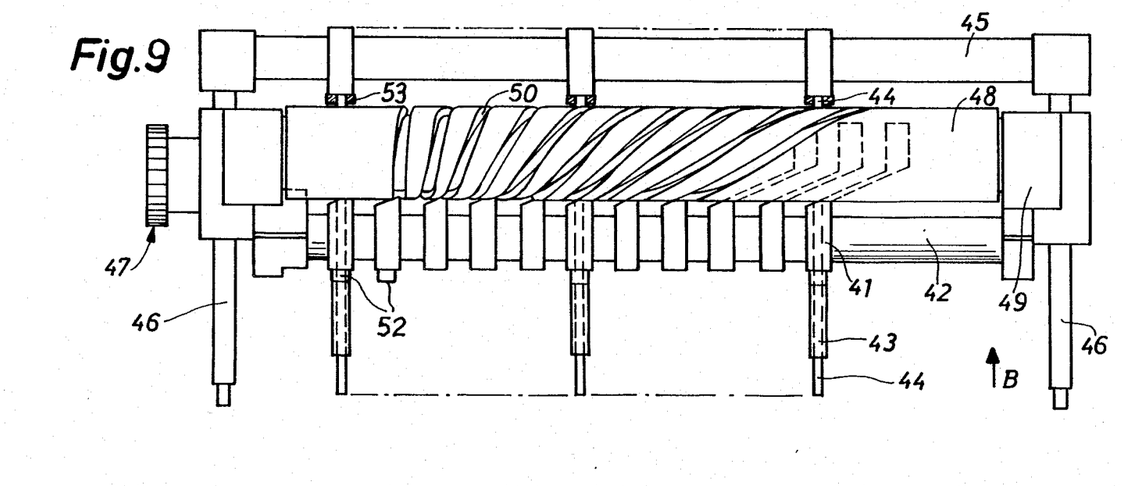
FIG. 9 is a side plan view of a part of a dosing device according to the present invention.
Figure 10:
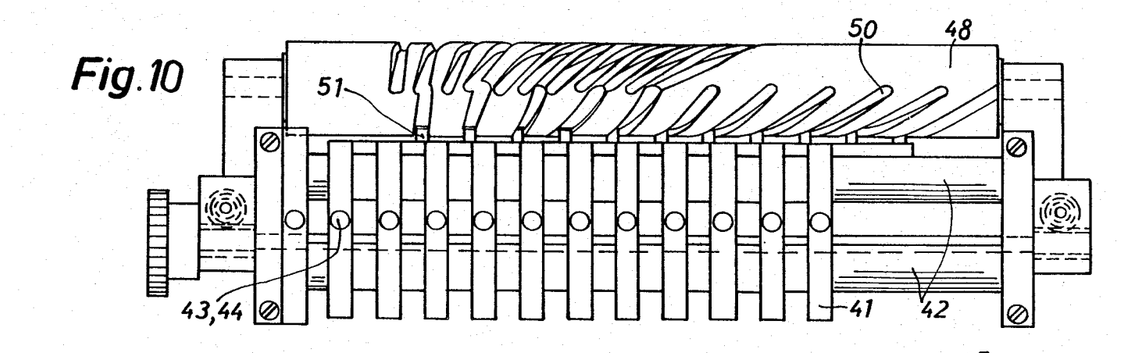
FIG. 10 is a plan veew of the dosing device viewed in the direction of arrow B in FIG. 9.

Preferably, dosing device 26 is equipped with twelve pickup devices 36 mounted thereon. FIGS. 9 and 10 show one part of dosing device 26. The dosing device effects, together with the displacement of the pipette or pipette piston, an adjustment of the distance between the adjacent pipettes so that the pipettes can be received with certainty from the slide; it can be perfectly inserted in the test container 31 and can be exactly centered in the individual recesses of the microstandard 22.

Dosing device 26 has a number of supports 41 guided by two parallel bars 42. On the supports 41, there are secured tubular connecting elements 43 on which there are respectively mounted, first gripping element 10 (FIG. 2) and outer collet 71 (FIG. 5a) of a pickup device 36. Through tubular connecting elements 43 and through supports 41, there extend second connecting elements 44 on which there are respectively mounted second gripping element 11 (FIG. 2) and inner collet 72 (FIG. 5b) of a pickup device 36. The second connecting elements are fastened on a bar 45 which, on both ends, are operatively connected, via racks 46, with a drive unit 47. By this drive unit 47, second connecting elements 44 are displaced in relation to the supports 41 and first connecting elements 43, and consequently, second gripping element 11 or inner collet 72 relative to first gripping element 10 or outer collet 71, and pipette piston 2 relative to pipette body 1. In addition, outer and inner collets 71 and 72 are respectively mounted via insulating elements 52 and 53 on first and second connecting elements 43 and 44, respectively. The pipettes are thereby electrically insulated in respect to the pipetting apparatus. To move the pipette or pipette body 1 in relation to chassis 25, there is provided another drive unit (not shown) that moves dosing device 26 as a whole.

To adjust the spacing between the pipettes, there is provided a roller 48 supported at opposite ends on bearings 49. Roller 48 comprises a number of helical grooves 50 formed on the periphery of roller 48. The initial and terminal points of helical grooves 50 are in one line that extends parallel to the axis of roller 48, and each of grooves 50 has a different inclination. Roller 48 is driven by a drive unit (not shown). Supports 41 are provided with attachments 51 that project into grooves 50, and thus, supports 41 are moved toward or away from each other by rotation of roller 48. Grooves 50 are shaped in a manner such that the distances between supports 41 and consequently between the pipettes, change uniformly.

Herein below is described a pipetting operation that can be performed with the above described pipetting apparatus.

By means of dosing device 26, pipettes 34 situated in slide 33 are received by means of pickup device 36. The number and arrangement of the pipettes are programmed in the control apparatus. Dosing device 26 conveys the pipettes to pickup device 21 of test containers 31. The test containers 31 are moved in the direction of dosing device 26 until the tips 8 and 65 of the pipette pistons (FIGS. 1 and 3) come into contact with the liquid. If the levels of the liquid in the test containers 31 are at the same height, the liquid is absorbed by the pipettes. The pipettes 36 are then moved for absorbing the reagents, the distance of the pipettes to the microstandard plate 22 being adapted at the same time, and the pipettes being externally cleansed in cleaning device 35. Thereafter the liquids absorbed by the pipettes are discharged, for instance, in the microstandard plates 22. Finally, pipettes 34 are ejected by dosing device 26 from pickup devices 36 into a waste container (not shown).

Other pipetting operations can also be performed together with the above described pipetting operation.

Having described specific preferred embodiments of the invention with reference to the accompanying drawings, it will be appreciated that the present invention is not limited to those precise embodiments, and that various changes and modifications may be effected therein by one of ordinary skill in the art without departing from the scope or spirit of the invention as defined in the appended claims.

What is claimed is:

1. A pipetting apparatus comprising:

a plurality of pipettes each having a pipette body having a first end section and;

a pipette piston positioned within the pipette body having a second end section;

the first and second end sections of the pipette body and the pipette piston forming a suction tip with substantially no clearance between the first and second end sections;

a portion of the second end section of the pipette piston extending beyond the first end section of the pipette body in a final position;

at least one of the pipette body and the pipette piston being electrically conductive, a pickup devices each including a first assembly for receiving the pipette body and a second assembly for receiving the pipette piston; means for moving the first and second assemblies; and at least one of the first and second assemblies being electrically conductive;

a first receiving device for receiving a plurality of test containers;

a second receiving device for receiving at least one assembly with vessels, which are arranged in a geometrically regular pattern;

a third feeding device for feeding pipettes from a pipette hopper to the pickup devices;

said first, second and third devices being fixedly arranged adjacent each other in a chassis and accessible from above;

a fourth dosing device provided with the pickup devices and movably disposed above said chassis in order to pick up pipettes in said third feeding device by means of the pickup devices, to absorb liquid from the containers in said first receiving device, and to discharge the absorbed liquid from the pipettes on said at least one assembly and then to eject the pipettes, said fourth device having one support for each pickup device, said supports being arranged side by side in a row, and adjusting means for proportionally adjusting the distance between said supports.

2. An apparatus according to claim 1, wherein said adjusting means includes a roller provided with a number of grooves and a drive unit for said roller, said grooves being helical in shape, each having a different inclination, and the initial and terminal points of said grooves are in a line that extends parallel with the axis of said roller, and said supports have attachments that mesh in said grooves.

3. An apparatus according to claim 1, wherein said first receiving device has a control unit including detectors formed in the pipettes to individually adjust the liquid level in the test containers to the same height as said fourth device.

4. An apparatus according to claim 3, wherein said first device has supports for the test containers and a drive means connected with said control unit and adapted to be operatively connected with said supports in order to individually move the test containers relative to said fourth device.

5. An apparatus according to claim 1, wherein said pipettes are arranged in a support element, and said third feeding device has a conveyor to transport said support elements with the pipettes from the pipette hopper, a displacement device to eject the pipettes from said support element, and a discharge means to prepare the pipettes for being received by the pickup devices.

6. An apparatus according to claim 5, wherein said displacement device and said discharge device respectively contain a drive controllable in a manner such that said displacement device selectively discharges pipettes in said discharge device.

7. An apparatus according to claim 1, wherein each support has a first connecting element to fasten said first assembly of a pickup device, and said fourth device contains an adjusting device that has second connecting elements to fasten said second assembly of of pickup device, and a drive unit to move said second connecting elements relative to said first connecting elements.

8. An apparatus according to claim 7, wherein a first and a second insulating element are respectively disposed between said first and said second connecting elements and said first and said second assemblies of the pickup device, in order to electrically insulate the pickup device with respect to said support.

9. A pipetting apparatus comprising:
- a plurality of pipettes each having a pipette body having a first and end section and
- a pipette piston positioned within the pipette body having a second end section;
- the first and second end sections of the pipette body and the pipette piston forming a suction tip with substantially no clearance between the first and second end sections;
- a portion of the second end section of the pipette piston extending beyond the first end section of the pipette body in a final position;
- at least one of the pipette body and the pipette piston being electrically conductive;
- a pickup devices each including a first assembly for receiving the pipette body and a second assembly for receiving the pipette piston; means for moving the first and second assemblies; and at least one of the first and second assemblies being electrically conductive;
- a first receiving device for receiving a plurality of individual test containers;
- a second receiving device for receiving at least one assembly with vessels, which are arranged in a geometrically regular pattern;
- a third feeding device for feeding pipettes from a pipette hopper to the pickup devices;
- said first, second and third devices being fixedly arranged adjacent each other in a chassis and accessible from above;
- a fourth closing device provided with the pickup devices and movably disposed above said chassis in order to pick up pipettes in said third feeding device by means of the pickup devices, to absorb liquid from the containers in said first receiving device, and to discharge the absorbed liquid from the pipettes on said at least one assembly and then to eject the pipettes, said fourth device being situated in a housing that is guided on one side thereof, said housing having a drive unit to move said fourth device above said chassis, said fourth device having one support for each pickup device and adjusting means for proportionally adjusting the distance between the pickup supports; and
- said first device having supports for the test containers and drive means operatively connected to the supports for individually moving the test containers relative to the fourth device.

* * * * *